US00PP25147P2

(12) United States Plant Patent
Takeuchi

(10) Patent No.: US PP25,147 P2
(45) Date of Patent: Dec. 2, 2014

(54) ***PETUNIA* PLANT NAMED 'KEISURFPUTEM'**

(50) Latin Name: *Petunia×hybrida*
Varietal Denomination: Keisurfputem

(71) Applicant: Shunsuke Takeuchi, Kozaki (JP)

(72) Inventor: Shunsuke Takeuchi, Kozaki (JP)

(73) Assignee: Keisei Rose Nurseries, Inc., Tokyo (JP)

( * ) Notice: Subject to any disclaimer, the term of this patent is extended or adjusted under 35 U.S.C. 154(b) by 69 days.

(21) Appl. No.: 13/815,274

(22) Filed: Feb. 15, 2013

(51) Int. Cl.
*A01H 5/00* (2006.01)

(52) U.S. Cl.
USPC ..... Plt./356.19

(58) Field of Classification Search
CPC ..... A01H 5/00
USPC ..... Plt./356.19
See application file for complete search history.

*Primary Examiner* — Anne Grunberg
(74) *Attorney, Agent, or Firm* — C. A. Whealy

(57) ABSTRACT

A new and distinct cultivar of *Petunia* plant named 'Keisurfputem', characterized by its mounding to trailing and decumbent plant habit; vigorous growth habit; freely branching and flowering plant habit; long flowering period; dark red purple-colored flowers; and good garden performance.

2 Drawing Sheets

Botanical designation: *Petunia×hybrida*.
Cultivar denomination: 'KEISURFPUTEM'.

BACKGROUND OF THE INVENTION

The present invention relates to a new and distinct cultivar of *Petunia* plant, botanically known as *Petunia×hybrida* and hereinafter referred to by the name 'Keisurfputem'.

The new *Petunia* plant is a product of a planned breeding program conducted by the Inventor in Katori, Chiba, Japan. The objective of the breeding program is to create new decumbent and freely flowering *Petunia* plants with early flowering habit and attractive flower coloration.

The new *Petunia* plant originated from a cross-pollination made by the Inventor in September, 2005 in Katori, Chiba, Japan of a proprietary selection of *Petunia×hybrida* identified as code number 06L-115, not patented, as the female, or seed, parent with a proprietary selection of *Petunia×hybrida* identified as code number 99L-16, not patented, as the male, or pollen, parent. The new *Petunia* plant was discovered and selected by the Inventor as a single flowering plant within the progeny of the stated cross-pollination in a controlled environment in Katori, Chiba, Japan in March, 2006.

Asexual reproduction of the new *Petunia* plant by terminal cuttings in a controlled environment in Katori, Chiba, Japan since March, 2006 has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Keisurfputem'. These characteristics in combination distinguish 'Keisurfputem' as a new and distinct cultivar of *Petunia* plant:

1. Mounding to trailing and decumbent plant habit.
2. Vigorous growth habit.
3. Freely branching and flowering plant habit.
4. Long flowering period.
5. Dark red purple-colored flowers.
6. Good garden performance.

Plants of the new *Petunia* can be compared to plants of the female parent selection. Plants of the new *Petunia* differ primarily from plants of the female parent selection in the following characteristics:

1. Plants of the new *Petunia* are broader than plants of the female parent selection.
2. Plants of the new *Petunia* have smaller flowers than plants of the female parent selection.
3. Plants of the new *Petunia* and the female parent selection differ in flower color as plants of the female parent selection have deep purple-colored flowers.

Plants of the new *Petunia* can be compared to plants of the male parent selection. Plants of the new *Petunia* differ primarily from plants of the male parent selection in the following characteristics:

1. Plants of the new *Petunia* are broader than plants of the male parent selection.
2. Plants of the new *Petunia* have smaller flowers than plants of the male parent selection.
3. Plants of the new *Petunia* and the male parent selection differ in flower color as plants of the male parent selection have purple-colored flowers.

Plants of the new *Petunia* can also be compared to plants of the *Petunia* 'Sunpurple', disclosed in U.S. Plant Pat. No. 16,358. In side-by-side comparisons conducted in Katori, Chiba, Japan, plants of the new *Petunia* and 'Sunpurple' differed primarily in the following characteristics:

1. Plants of the new *Petunia* were shorter and broader than plants of 'Sunpurple'.
2. Plants of the new *Petunia* had shorter internodes than plants of 'Sunpurple'.
3. Plants of the new *Petunia* had smaller leaves than plants of 'Sunpurple'.

4. Plants of the new *Petunia* had smaller flowers than plants of 'Sunpurple'.
5. Plants of the new *Petunia* had smaller sepals than plants of 'Sunpurple'.
6. Plants of the new *Petunia* had longer peduncles than plants of 'Sunpurple'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet comprises a side perspective view of a typical flowering plant of 'Keisurfputem' grown in a container.

The photograph on the second sheet is a close-up view of a typical flowering plant of 'Keisurfputem'.

DETAILED BOTANICAL DESCRIPTION

The aforementioned photographs and following observations, measurements and values describe plants grown during the late summer and early autumn in 9-cm containers in a glass-covered greenhouse in Katori, Chiba, Japan and under cultural practices typical of commercial production. During the production of the plants, day temperatures averaged 21° C. and night temperatures averaged 14° C. Plants were pinched one time and were four months old when the photographs and description were taken. In the following description, color references are made to The Royal Horticultural Society Colour Chart, 2007 Edition, except where general terms of ordinary dictionary significance are used.

Botanical classification: *Petunia×hybrida* 'Keisurfputem'.

Parentage:

*Female, or seed, parent*.—Proprietary selection of *Petunia×hybrida* identified as code number 06L-115, not patented.

*Male, or pollen, parent*.—Proprietary selection of *Petunia×hybrida* identified as code number 99L-16, not patented.

Propagation:

*Type*.—By terminal cuttings.

*Time to initiate roots, summer*.—About one week at temperatures of 15° C. to 30° C.

*Time to initiate roots, winter*.—About three weeks at temperatures of 15° C.

*Time to produce a rooted young plant, summer*.—About four weeks at temperatures of 15° C. to 30° C.

*Time to produce a rooted young plant, winter*.—About four weeks at temperatures of 15° C.

*Root description*.—Fibrous, medium in thickness; white in color.

*Rooting habit*.—Freely branching; medium density.

Plant description:

*Plant and growth habit*.—Mounding to trailing and decumbent plant habit; freely branching habit with numerous lateral branches developing per plant; pinching enhances lateral branch development; vigorous growth habit.

*Plant height*.—About 8.8 cm.

*Plant diameter*.—About 38 cm.

Lateral branch description:

*Length*.—About 20.7 cm.

*Diameter*.—About 1.5 mm.

*Internode length*.—About 1.1 cm.

*Strength*.—Strong, flexible.

*Aspect*.—Trailing and decumbent.

*Texture*.—Pubescent.

*Color*.—Close to 143C.

Foliage description:

*Arrangement*.—Alternate, simple.

*Length*.—About 5.1 cm.

*Width*.—About 2.5 cm.

*Shape*.—Elliptic.

*Apex*.—Acute.

*Base*.—Attenuate.

*Margin*.—Entire.

*Texture, upper and lower surfaces*.—Pubescent.

*Venation pattern*.—Pinnate; reticulate.

*Color*.—Developing leaves, upper surface: Close to 141A. Developing leaves, lower surface: Close to 141B. Fully expanded leaves, upper surface: Close to 136B; venation, close to 144C. Fully expanded leaves, lower surface: Close to 143A; venation, close to 144C.

*Petioles*.—Length: About 1.1 cm. Diameter: About 1.5 mm. Texture, upper and lower surfaces: Pubescent. Color, upper and lower surfaces: Close to 143C.

Flower description:

*Flower arrangement and habit*.—Single salverform flowers arising from upper leaf axils; freely flowering habit typically with numerous flowers developing per plant; flowers face upright to outwardly.

*Fragrance*.—Faintly fragrant; pleasant.

*Natural flowering season*.—Early flowering habit, plants of the new *Petunia* initiate and develop flowers about two to three weeks after planting; long flowering period; flowering commences naturally in the spring, flowering continuous throughout the summer until late autumn in Japan.

*Flower longevity*.—Individual flowers last about five days on the plant; flowers persistent.

*Flower diameter*.—About 5.3 cm.

*Flower length (depth)*.—About 3.8 cm.

*Flower buds*.—Length: About 2.8 cm. Diameter: About 5.8 mm. Shape: Cylindrical; apex, twisted. Color: Close to 79B.

*Corolla*.—Arrangement: Five petals fused at the base and opening into a flared trumpet. Petal length from throat: About 2.5 cm. Petal width: About 2.9 cm. Petal shape: Roughly spatulate. Petal apex: Obtuse. Petal margin: Entire; undulate. Petal texture, upper and lower surfaces: Smooth, glabrous; satiny. Throat texture: Smooth, glabrous. Tube texture: Pubescent. Color: Petal, when opening, upper surface: Close to 80A. Petal, when opening, lower surface: Close to 80B. Petal, fully opened, upper surface: Close to N74A; venation, close to 79A; color becoming closer to 77A with development. Petal, fully opened, lower surface: Close to N74C; venation, close to 79B. Throat: Close to N74B; venation, close to 79A. Tube: Close to 77C; venation, close to 79B.

*Calyx*.—Arrangement: Tubular star-shaped calyx tube with five sepals fused at the base. Sepal length: About 1.6 cm. Sepal width: About 4.5 mm. Sepal shape: Narrowly elliptic. Sepal apex: Broadly acute. Sepal margin: Entire. Sepal texture, upper and lower surfaces: Pubescent. Color, immature and mature, upper surface: Close to 137B. Color, immature and mature, lower surface: Close to 143A.

*Peduncles*.—Length: About 2 cm. Diameter: About 1.5 mm. Strength: Strong. Texture: Pubescent; viscid. Color: Close to 143B.

*Reproductive organs*.—Stamens: Quantity per flower: Five. Anther size: About 1 mm by 1 mm. Anther shape: Roughly round. Anther color: Close to 97B. Pollen amount: Moderate. Pollen color: Close to 97D. Pistils: Quantity per flower: One. Pistil length: About 1.6 cm. Style length: About 1.4 cm. Style color: Close to 144C. Stigma shape: Roughly round. Stigma color: Close to 144A. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Keisurfputem' as illustrated and described.

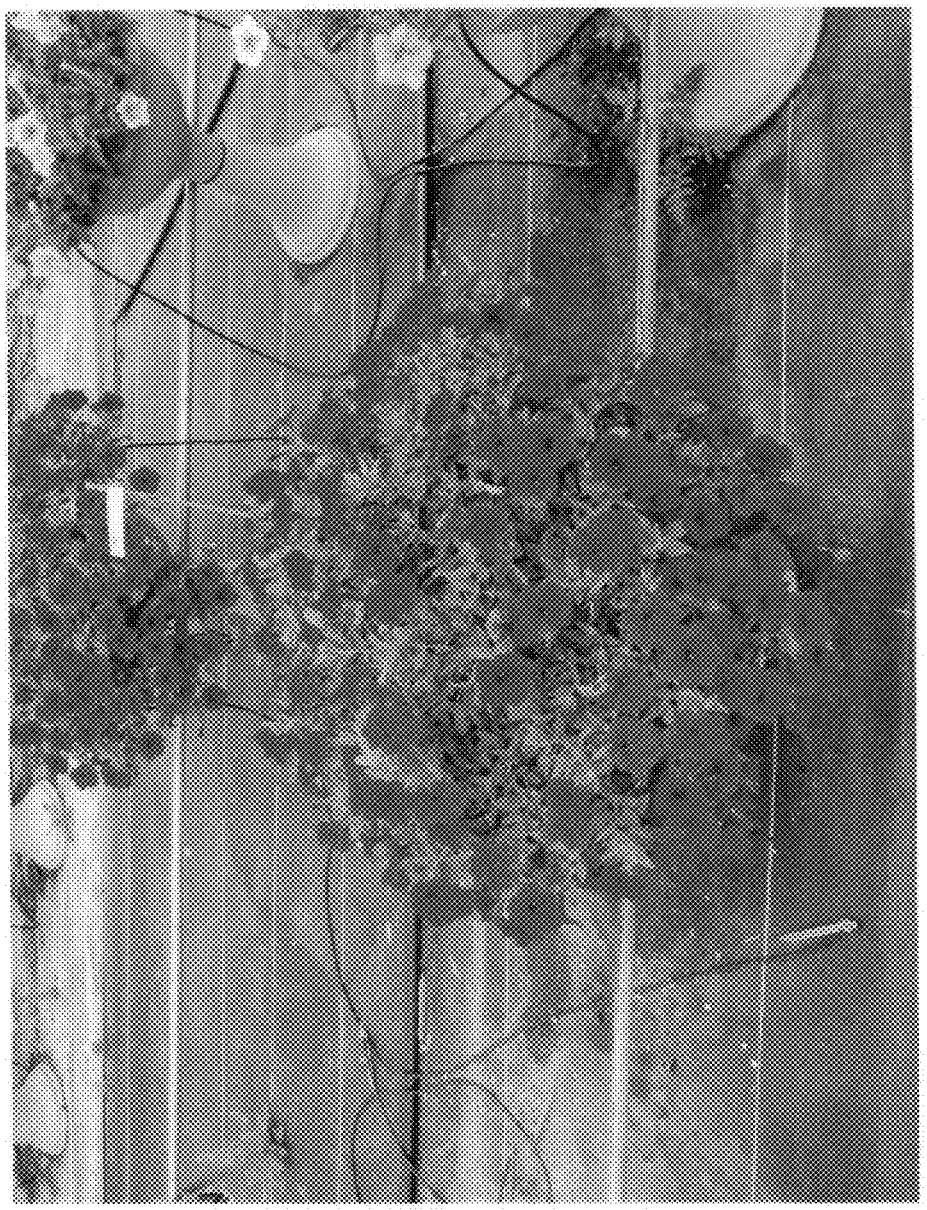

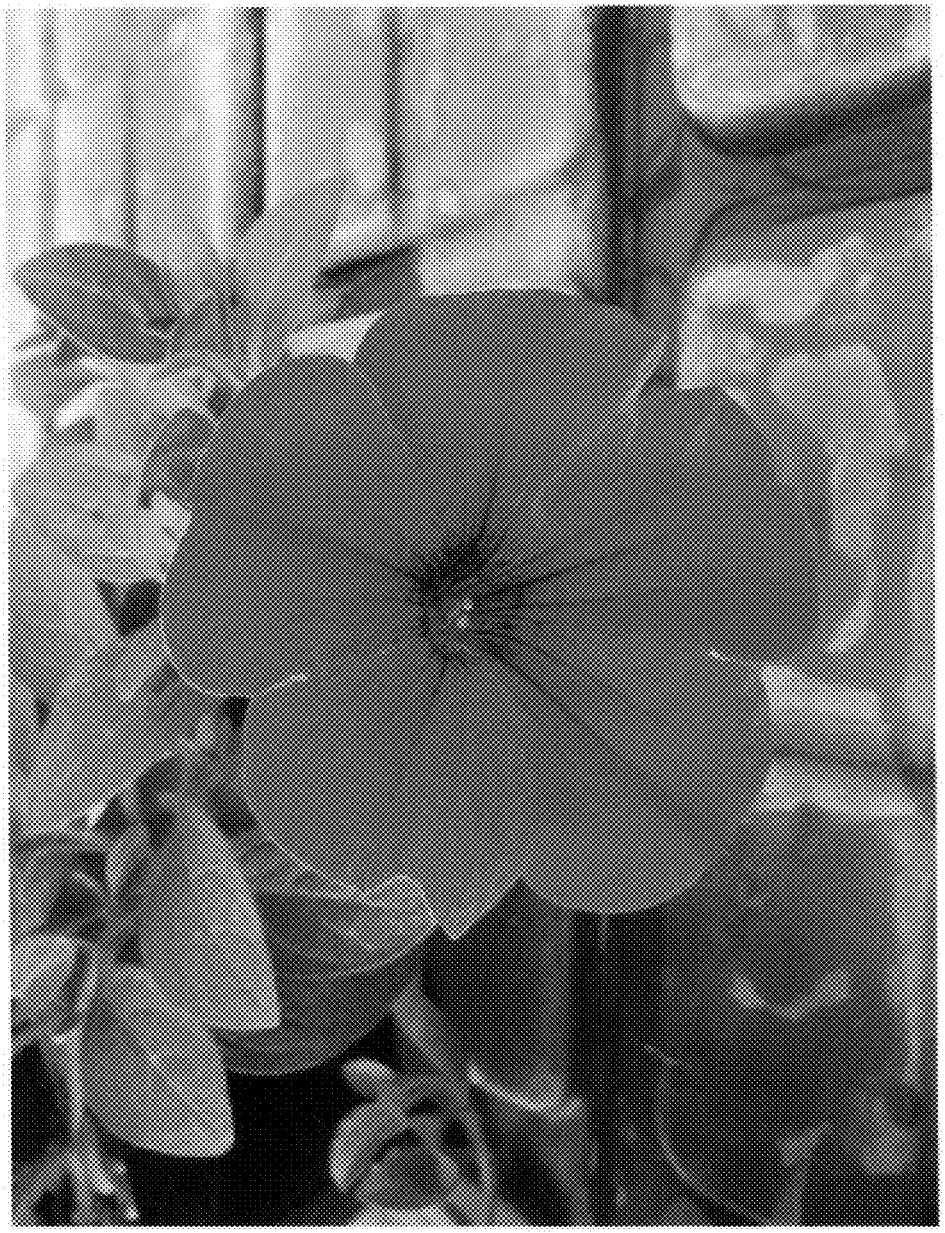

* * * * *